(12) United States Patent
Dai et al.

(10) Patent No.: US 7,811,572 B2
(45) Date of Patent: *Oct. 12, 2010

(54) PROCESS FOR PREPARING PURIFIED DRUG CONJUGATES

(75) Inventors: Yong Dai, Newton, MA (US); Yong Wang, North Attleboro, MA (US); Shengjin Jin, Acton, MA (US); Deborah H. Meshulam, Brookline, MA (US); Godfrey W. Amphlett, Cambridge, MA (US)

(73) Assignee: ImmunoGen, Inc., Waltham, MA (US)

( * ) Notice: Subject to any disclaimer, the term of this patent is extended or adjusted under 35 U.S.C. 154(b) by 315 days.

This patent is subject to a terminal disclaimer.

(21) Appl. No.: 11/503,781

(22) Filed: Aug. 14, 2006

(65) Prior Publication Data

US 2007/0048314 A1 Mar. 1, 2007

Related U.S. Application Data

(60) Provisional application No. 60/710,858, filed on Aug. 24, 2005, provisional application No. 60/797,713, filed on May 4, 2006.

(51) Int. Cl.
*A61K 39/395* (2006.01)
*G01N 33/53* (2006.01)
*C07K 16/28* (2006.01)

(52) U.S. Cl. .......... 424/178.1; 424/145.1; 424/155.1; 424/183.1; 530/387.7; 530/388.23; 530/391.7

(58) Field of Classification Search .................. None
See application file for complete search history.

(56) References Cited

U.S. PATENT DOCUMENTS

| | | | |
|---|---|---|---|
| 4,149,003 A | 4/1979 | Carlsson et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,664,911 A | 5/1987 | Uhr et al. |
| 5,024,834 A | 6/1991 | Houston et al. |
| 5,208,020 A | 5/1993 | Chari et al. |
| 5,225,539 A | 7/1993 | Winter |
| 5,241,078 A | 8/1993 | Moreland et al. |
| 5,416,064 A | 5/1995 | Chari et al. |
| 5,475,092 A | 12/1995 | Chari et al. |
| 5,545,806 A | 8/1996 | Lonberg et al. |
| 5,552,293 A | 9/1996 | Lindholm et al. |
| 5,569,825 A | 10/1996 | Lonberg et al. |
| 5,580,853 A | 12/1996 | Sytkowski |
| 5,585,089 A | 12/1996 | Queen et al. |
| 5,585,499 A | 12/1996 | Chari et al. |
| 5,639,641 A | 6/1997 | Pedersen et al. |
| 5,665,357 A | 9/1997 | Rose et al. |
| 5,693,761 A | 12/1997 | Queen et al. |
| 5,693,762 A | 12/1997 | Queen et al. |
| 5,714,352 A | 2/1998 | Jakobovits |
| 5,846,545 A | 12/1998 | Chari et al. |
| 5,885,793 A | 3/1999 | Griffiths et al. |
| 5,969,108 A | 10/1999 | McCafferty et al. |
| 6,171,586 B1 | 1/2001 | Lam et al. |
| 6,265,150 B1 | 7/2001 | Terstappen et al. |
| 6,333,410 B1 | 12/2001 | Chari et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,441,163 B1 | 8/2002 | Chari et al. |
| 6,534,660 B1 | 3/2003 | Yongxin et al. |
| 6,586,618 B1 | 7/2003 | Zhao et al. |
| 6,596,757 B1 | 7/2003 | Chari et al. |
| 6,630,579 B2 | 10/2003 | Chari et al. |
| 6,706,708 B2 | 3/2004 | Chari et al. |
| 6,716,821 B2 | 4/2004 | Zhao et al. |
| 6,756,397 B2 | 6/2004 | Zhao et al. |
| 7,045,605 B2 | 5/2006 | Bander et al. |
| 2002/0197266 A1 | 12/2002 | Debinski |
| 2003/0004210 A1 | 1/2003 | Chari et al. |

(Continued)

FOREIGN PATENT DOCUMENTS

EP 0 239 400 A2 9/1987

(Continued)

OTHER PUBLICATIONS

Boschetti, E., Antibody separation by hydrophobic charge induction chromatography, 2002, TRENDS in Biotechnology, vol. 20, Issue 8, pp. 333-337.*

(Continued)

*Primary Examiner*—Robert Landsman
*Assistant Examiner*—Ian Dang
(74) *Attorney, Agent, or Firm*—Leydig, Voit & Mayer, Ltd.

(57) ABSTRACT

The invention provides a process for preparing a cell-binding agent chemically coupled to a drug. The process comprises covalently attaching a linker to a cell-binding agent, a purification step, conjugating a drug to the cell-binding agent and a subsequent purification step.

40 Claims, No Drawings

U.S. PATENT DOCUMENTS

| | | | |
|---|---|---|---|
| 2003/0195365 A1 | 10/2003 | Zhao et al. |
| 2004/0024049 A1 | 2/2004 | Baloglu et al. |
| 2004/0235840 A1 | 11/2004 | Chari et al. |
| 2004/0241174 A1 | 12/2004 | Amphlett et al. |
| 2005/0118183 A1 | 6/2005 | Hoffee et al. |
| 2005/0169933 A1 | 8/2005 | Steeves et al. |
| 2005/0175619 A1 | 8/2005 | Duffy et al. |
| 2006/0182750 A1 | 8/2006 | Chari et al. |
| 2006/0233811 A1 | 10/2006 | Chari |

FOREIGN PATENT DOCUMENTS

| | | |
|---|---|---|
| EP | 0 425 235 A2 | 5/1991 |
| GB | 2 188 638 A | 10/1987 |
| WO | WO 92/01047 A1 | 1/1992 |
| WO | WO 99/06587 A2 | 2/1999 |
| WO | WO 00/02587 A1 | 1/2000 |
| WO | WO 01/24763 A2 | 4/2001 |
| WO | WO 02/16401 A2 | 2/2002 |
| WO | WO 02/060955 A2 | 8/2002 |
| WO | WO 02/092127 A1 | 11/2002 |
| WO | WO 02/094325 A2 | 11/2002 |
| WO | WO 02/098897 A2 | 12/2002 |
| WO | WO 03/053462 A2 | 7/2003 |
| WO | WO 03/057163 A2 | 7/2003 |
| WO | WO 03/102132 A2 | 12/2003 |
| WO | WO 2004/103272 A2 | 12/2004 |
| WO | WO 2005/037992 A2 | 4/2005 |
| WO | WO 2005/077090 A2 | 8/2005 |
| WO | WO 2005/094882 A | 10/2005 |
| WO | WO 2005/117986 A2 | 12/2005 |
| WO | WO 2006/113623 A2 | 10/2006 |

OTHER PUBLICATIONS

Christy et al., *Desalination*, 144(1-3): 133-136 (2002).
Okamoto et al., *JP J. Cancer Research*, 83(7): 761-768 (1992).
Bhuyan et al., *Cancer Research*, 42[9]: 3532-3537 (1982).
Boger et al., *Bioorg. Med. Chem. Lett.*, 1: 115-120 (1991).
Boger et al., *J. Org. Chem.*, 55: 5823-5833 (1990).
Burgess, *Immunology Today*, 5[6]: 155-158 (1984).
Chari et al., Cancer Research, 52[1]: 127-131 (1992).
Chari et al, Cancer Research 55[18]: 4079-4084 (1995).
Colomer et al, *Cancer Invest.*, 19[1]: 49-56 (2001).
Desmyter et al., *Nature Struct. Biol.*, 3[9]: 803-811 (1996).
Ghetie et al., *J. Immunological Methods*, 111[2]: 267-277 (1988).
Greenberg et al, *Nature*, 374: 168-173 (1995).
Griffin et al., *Leukemia Res.*, 8[4]: 521-534 (1984).
Haskard et al., *J. Immunol. Methods*, 74[2]: 361-367 (1984).
Heider et al., *Eur. J. Cancer*, 31A[13/14]: 2385-2391 (1995).
Huse et al., *Science*, 246: 1275-1281 (1989).
Kohler et al., *Eur. J. Immunol.*, 6: 511-519 (1976).
Liu et al., *Proc. Natl. Acad. Sci. USA*, 93: 8618-8623 (1996).
Liu et al., *Cancer Res.*, 57[17]: 3629-3634 (1997).
Maloney et al., *Blood*, 90[6]: 2188-2195 (1997).
Nadler et al., *J. Immunol.*, 131: 244-250 (1983).
Nisonoff et al., *Arch. Biochem. Biophys.*, 89: 230-244 (1960).
O'Keefe et al., *J. Biol. Chem.*, 260[1]: 932-937 (1985).
Parham, *J. Immunol.*, 131: 2895-2902 (1983).
Pedersen et al., *J. Mol. Biol.*, 235: 959-973 (1994).
Ritz et al., *Nature*, 283: 583-585 (1980).
Roder et al., *Methods Enzymol*, 121: 140-167 (1986).
Roguska et al., *Proc. Natl. Acad. Sci. USA*, 91: 969-973 (1994).
Spring et al., *J. Immunol.*, 113: 470-478 (1974).
Stanfield et al., *Science*, 305: 1770-1773 (2004).
Taylor-Papadimitriou et al., *Int. J. Cancer*, 25: 17-21 (1981).
Trouet et al., *Proc. Natl. Acad. Sci. USA*, 79: 626-629 (1982).
Umemoto et al., *Int. J. Cancer*, 43[4]: 677-684 (1989).
Van Hof et al., *Cancer Res.* 56[22]: 5179-5185 (1996).
Warpehoski et al., *J. Med. Chem*, 31: 590-603 (1988).
Welt et al., *J. Clin. Oncol.*, 12[6]: 1193-1203 (1994).
Carlsson et al., *Biochem. J.*, 173: 723-737 (1978).
Reider et al., *The Alkaloids*, XXIII: 71-73 (1984).
Reiter et al., *Protein Engineering*, 7: 697-704 (1994).
Sytkowski et al., *Proc. Natl. Acad. Sci. USA*, 95: 1184-1188 (1998).

\* cited by examiner

PROCESS FOR PREPARING PURIFIED DRUG CONJUGATES

CROSS-REFERENCE TO RELATED INVENTIONS

This patent application claims the benefit of U.S. Provisional Patent Application No. 60/710,858, filed Aug. 24, 2005, and U.S. Provisional Patent Application 60/797,713, filed May 4, 2006.

FIELD OF THE INVENTION

This invention pertains to a process for preparing conjugates of substantially high purity and stability, wherein the conjugates comprise a cell-binding agent chemically coupled to a drug.

BACKGROUND OF THE INVENTION

The treatment of cancer has progressed significantly with the development of pharmaceuticals that more efficiently target and kill cancer cells. To this end, researchers have taken advantage of cell-surface receptors and antigens selectively expressed by cancer cells to develop drugs based on antibodies that bind the tumor-specific or tumor-associated antigens. In this regard, cytotoxic molecules such as bacteria and plant toxins, radionuclides, and certain chemotherapeutic drugs have been chemically linked to monoclonal antibodies that bind tumor-specific or tumor-associated cell surface antigens (see, e.g., International Patent Applications WO 00/02587, WO 02/060955, and WO 02/092127, U.S. Pat. Nos. 5,475,092, 6,340,701, and 6,171,586, U.S. Patent Application Publication No. 2003/0004210 A1, and Ghetie et al., *J. Immunol. Methods*, 112: 267-277 (1988)). Such compounds are typically referred to as toxin, radionuclide, and drug "conjugates," respectively. Often they also are referred to as immunoconjugates, radioimmunoconjugates, and immunotoxins. Tumor cell killing occurs upon binding of the drug conjugate to a tumor cell and release or/and activation of the cytotoxic activity of the drug. The selectivity afforded by drug conjugates minimizes toxicity to normal cells, thereby enhancing tolerability of the drug in the patient.

Processes for conjugating antibodies to sulfhydryl-containing cytotoxic agents such as maytansinoids have been described previously (see, e.g., U.S. Pat. Nos. 5,208,020, 5,416,064, and 6,441,163). For example, U.S. Pat. Nos. 5,208,020 and 5,416,064 disclose a process for manufacturing antibody-maytansinoid conjugates wherein the antibody is first modified with a heterobifunctional reagent such as described in U.S. Pat. Nos. 4,149,003, 4,563,304 and U.S. Patent Application Publication No. 2004/0241174 A1. U.S. Pat. Nos. 5,208,020 and 5,416,064 further describe conjugation of a modified antibody with an excess of a sulflhydryl-containing cytotoxic agent at pH 7, followed by purification on Sephadex™ G25 chromatography columns. Purification of antibody-drug conjugates by size exclusion chromatography (SEC) also has been described (see, e.g., Liu et al., *Proc. Natl. Acad. Sci.* (*USA*), 93: 8618-8623 (1996), and Chari et al., *Cancer Research*, 52: 127-131 (1992)).

The processes that have been previously described for manufacture of the antibody-drug conjugates are complex because they are encumbered with steps that are cumbersome to perform or produce immunoconjugates that are less pure or less stable than optimally desired. For example, conjugation at a pH of between 6.0 and 6.5 is not optimal for producing pure and stable conjugates. In addition, the conjugation reactions under these conditions are generally slow and inefficient, leading to a requirement for excessive time and material usage.

It would be desirable to modify or eliminate one or more manufacturing steps without compromising product quality, such as purity and/or stability. It would be further desirable to have additional purification options than those that have been so far described inasmuch as some options will be more efficacious with certain combinations of cell binding agents, linkers, and drugs, than with others.

In view of the foregoing, there is a need in the art to develop improved methods of preparing cell-binding agent-drug conjugate compositions that are of substantially high purity and at the same time have greater stability. The invention provides such a method. These and other advantages of the invention, as well as additional inventive features, will be apparent from the description of the invention provided herein.

BRIEF SUMMARY OF THE INVENTION

The invention provides a process for preparing a conjugate of substantially high purity and stability comprising a cell-binding agent chemically coupled to a drug. The process comprises (a) contacting a cell-binding agent with a bifunctional crosslinking reagent to covalently attach a linker to the cell-binding agent and thereby prepare a first mixture comprising cell-binding agents having linkers bound thereto, (b) subjecting the first mixture to tangential flow filtration, adsorptive chromatography, adsorptive filtration, selective precipitation, or combination thereof, and thereby prepare a purified first mixture of cell-binding agents having linkers bound thereto, (c) conjugating a drug to the cell-binding agents having linkers bound thereto in the purified first mixture by reacting the cell-binding agents having linkers bound thereto with a drug in a solution having a pH of about 4 to about 9 to prepare a second mixture comprising (i) cell-binding agent chemically coupled through the linker to the drug, (ii) free drug, and (iii) reaction by-products, and (d) subjecting the second mixture to tangential flow filtration, adsorptive chromatography, adsorptive filtration, selective precipitation, or combination thereof to purify the cell-binding agents chemically coupled through the linkers to the drug from the other components of the second mixture and thereby prepare a purified second mixture.

DETAILED DESCRIPTION OF THE INVENTION

The invention provides a process for preparing cell-binding agent-drug conjugates of substantially high purity and stability. Such compositions can be used for treating diseases because of the high purity and stability of the conjugates. Compositions comprising a cell-binding agent, such as an antibody, chemically coupled to a drug, such as a maytansinoid, are described in, for example, U.S. Patent Application Publication No. 2004/0241174 A1. In this context, substantially high purity is considered to be: (a) greater than 90%, preferably greater than 95%, of conjugate species are monomeric, and/or (b) free drug level in the conjugate preparation is less than 2% (relative to total drug).

In this respect, the inventive process comprises (a) modifying the cell-binding agent with a bifunctional crosslinking reagent to covalently attach a linker to the cell-binding agent and thereby prepare a first mixture comprising cell-binding agents having linkers bound thereto, (b) subjecting the first mixture to tangential flow filtration, adsorptive chromatography, adsorptive filtration, selective precipitation, or combinations thereof, to purify the cell-binding agents having linkers bound thereto from other components of the first mixture and thereby prepare a purified first mixture of cell-binding agents having linkers bound thereto, (c) conjugating a drug to the cell-binding agents having linkers bound thereto in the purified first mixture by reacting the cell-binding agents having linkers bound thereto with the drug in a solution having a pH of about 4 to about 9 to prepare a second mixture comprising (i) cell-binding agent chemically coupled through the linker to the drug, (ii) free drug, and (iii) reaction by-products, and (d) subjecting the second mixture to tangential flow filtration, adsorptive chromatography, adsorptive filtration, selective precipitation, or combination thereof, to remove the non-conjugated drugs, reactants, and by-products, as well as to obtain substantially purified cell-binding agent-drug conjugates. Optionally, the inventive process further comprises holding the mixture between at least one of steps a-b, steps b-c, and/or steps c-d to release the unstably bound linkers from the cell binding agent.

Preferably, tangential flow filtration (TFF, also known as cross flow filtration, ultrafiltration and diafiltration) and/or adsorptive chromatography resins are utilized in the purification steps. However, when TFF is used in the first purification step (step b), in (step c), a conjugation at pH of 6.0-6.5 is used, and an adsorptive chromatography resin is utilized in the second purification step (step d), it is preferred that the adsorptive chromatography resin is a non-ion exchange resin. In other preferred embodiments, TFF is utilized in both purification steps, or adsorptive chromatography resins are utilized in both purification steps. Alternatively, an adsorptive chromatography resin is utilized in the first purification step, and TFF is utilized in the second purification step. A combination of TFF and an adsorptive chromatography resin can be utilized in the first and/or second purification step as well.

Any suitable TFF systems may be utilized, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized. Preferred adsorptive chromatography resins include resins for hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), where the cell binding agent is an antibody, and lectin affinity resins, e.g. Lentil Lectin Sepharose resin (GE Healthcare, Piscataway, N.J.), where the cell binding agent bears appropriate lectin binding sites. Alternatively an antibody specific to the cell binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

In accordance with the inventive method, a first mixture is produced comprising the cell-binding agent having linkers bound thereto, as well as reactants and other by-products. Purification of the modified cell-binding agent from reactants and by-products is carried out by subjecting the first mixture to a purification process. In this regard, the first mixture can be purified using tangential flow filtration (TFF), e.g., a membrane-based tangential flow filtration process, adsorptive chromatography, adsorptive filtration, or selective precipitation, or any other suitable purification process, as well as combinations thereof. This first purification step provides a purified first mixture, i.e., an increased concentration of the cell-binding agents having linkers bound thereto and a decreased amount of unbound bifunctional crosslinking reagent, as compared to the first mixture prior to purification in accordance with the invention.

After purification of the first mixture to obtain a purified first mixture of cell-binding agents having linkers bound thereto, a drug is conjugated to the cell-binding agents having linkers bound thereto in the first purified mixture by reacting the cell-binding agents having linkers bound thereto with a drug in a solution having a pH from about 4 to about 9, whereupon a second mixture comprising (i) the cell-binding agent chemically coupled through the linker to the drug, (ii) free drug, and (iii) reaction by-products is produced. While the conjugation reaction is performed at a pH of about 4 to about pH 9, the reaction is preferably performed at a pH of about 6 or below or at a pH of about 6.5 or greater, most preferably at a pH of about 4 to about 6 or at a pH of about 6.5 to about 9, and especially at a pH of 4 to less than 6 or at a pH of greater than 6.5 to 9. When the conjugation step is performed at a pH of about 6.5 or greater, some sulhydryl-containing drugs may be prone to dimerize by disulfide-bond formation. Removal of trace metals and/or oxygen from the reaction mixture, as well as optional addition of antioxidants or the use of linkers with more reactive leaving groups, or addition of drug in more than one aliquot, may be required to allow for efficient reaction in such a situation.

Optionally, purification of the modified cell binding agent may be omitted. In such a situation, the drug may be added simultaneously with the crosslinking reagent or at some later point, e.g., 1, 2, 3, or more hours after addition of the crosslinking reagent to the cell binding agent.

The inventive method may optionally include the addition of sucrose to the conjugation step used in the inventive method to increase solubility and recovery of the cell-binding agent-drug conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to 10% (w/v) (e.g., about 2% (w/v), about 4% (w/v), about 6% (w/v), or about 8% (w/v)). In addition, the conjugation reaction also can comprise the addition of a buffering agent. Any suitable buffering agent known in the art can be used. Suitable buffering agents include, for example, a citrate buffer, an acetate buffer, a succinate buffer, and a phosphate buffer.

Following the conjugation step, the second mixture is subjected to a purification step. In this regard, the second mixture can be purified using tangential flow filtration (TFF), e.g., a membrane-based tangential flow filtration process, adsorptive chromatography, absorptive filtration, selective precipitation, or any other suitable purification process, as well as combinations thereof, which are set-forth herein. This second purification step provides a purified second mixture, i.e., an increased concentration of the cell-binding agents chemically coupled through the linkers to the drug and a decreased amount of one or more other components of the second mixture, as compared to the second mixture prior to purification in accordance with the invention.

The inventive process optionally further comprises a holding step after modification of the cell binding agent with a bifunctional crosslinking reagent. The holding step comprises maintaining the solution at a suitable temperature for a suitable period of time to release the unstably bound linkers from the cell binding agent while not substantially releasing the stably bound linkers from the cell binding agent. Desirably, the holding step comprises maintaining the solution at a temperature of about 2° C. to about 8° C. for a period of at least about 12 hours for up to 30 days or more. Alternatively, the duration of the holding step can be substantially reduced by performing the holding step at elevated temperature, with the maximum temperature limited by the stability of the cell binding agent-drug conjugate. For example, for an antibody-drug conjugate the holding step can be performed at up to about 37° C. for up to about four weeks, preferably, between two to four weeks, even more preferably, between one and two weeks, and most preferably for about one week or less (e.g., 2 hours to about six days). Preferred pH values for the holding step range from about 6-10. Most preferred pH values are between about 6.5 and 8.5. Preferably, the holding step comprises incubating the mixture comprising the modified cell binding agent at 4° C. at pH 6.5 for at least about 12 hours to 4 weeks. More preferably, the holding step comprises incubating the mixture comprising the modified cell binding agent at a range between 20-30° C. at pH 6.5 for about 12 hours to about 1 week. The holding step can be performed before or after the cell binding agent is conjugated to the drug. Preferably, the holding step is performed directly after the modification of the cell binding agent with the bifunctional crosslinking reagent.

In an embodiment, the inventive process comprises a holding step after modification of the cell binding agent with a bifunctional crosslinking reagent and before conjugation. The holding step comprises maintaining the solution at a suitable temperature for a suitable period of time to release the unstably bound linkers from the cell binding agent while not substantially releasing the stably bound linkers from the cell binding agent. Desirably, the holding step comprises maintaining the solution at a temperature of about 2° C. to about 8° C. for a period of at least about 5 hours for up to 5 days or more, for example 30 days. Alternatively, the duration of the holding step can be substantially reduced by performing the holding step at elevated temperature, with the maximum temperature limited by the stability of the cell binding agent-drug conjugate. For example, for an antibody-drug conjugate the holding step can be performed at up to about 37° C. for up to about four weeks, preferably between one to four weeks, even more preferably, between two to four weeks, and most preferably for about one week or less (e.g., 2 hours to about six days). The pH value for the holding step preferably is about 4 or more, but less than about 6 (e.g., 4-5.9). The pH value for the holding step more preferably is about 5 or more, but less than about 6 (e.g., 5-5.9). Preferably, the holding step comprises incubating the mixture comprising the modified cell binding agent at 4° C. at pH 5 for at least about 5 hours for up to 5 days or more, for example 10 days. More preferably, the holding step comprises incubating the mixture comprising the modified cell binding agent at a range between 20-30° C. at a pH of about 5 for about 5 hours to about 1 to 3 days, preferably 1 day. After modification of the cell binding agent, a purification step may be performed before the hold step and/or after the hold step, but prior to the conjugation step. Such purification steps, such as non-adsorptive or adsorptive chromatography, are well known to one of ordinary skill in the art.

In an embodiment, the duration of the holding step can be substantially reduced by the addition of nucleophiles. The nucleophiles can be added during the conjugation step and the holding step can performed simultaneously with conjugation. In the context of the invention, nucleophiles are chemical moieties that can react with ester groups and imidazole amides on modified cell binding agents in aqueous solutions. Suitable nucleophiles are known in the art and include, for example, primary amines, i.e., $RNH_2$, where R is an alkyl or aromatic group; or secondary amines, i.e., RR'NH, where R and R' are alkyl or aromatic groups. Amines also can be amino acids, peptides containing lysine amino acids, peptides containing alpha-amino or non-natural secondary amino groups, or water-soluble amines. Nucleophiles can be in solution, in a polymeric state, or in an immobilized form as a solid phase reagent. Examples of suitable nucleophiles in solution include, but are not limited to, glycylglycine, glycine, taurine (sodium 2-aminoethanesulfonate), ethanolamine, diethanolamine, lysine, hydroxylamine, hydrazine, imidazole, histidine, ethylamine, 2-amino-2-(hydroxymethyl)-1,3-propanediol and 4-amino-1-butanol. Appropriate concentrations of soluble nucleophiles range from about 0.1 mM to the limit of solubility for the particular nucleophile. Examples of nucleophiles in a polymeric state include, but are not limited to, poly(ethyleneimine), poly-lysine, and peptides with lysine amino acids and peptides containing alpha-amino or non-natural secondary amino groups. Examples of nucleophiles in immobilized form as a solid phase reagent include, but are not limited to, solid phase linked amines, such as EAH Sepharose 4B and aminomethyl polystyrene beads. For a solid phase nucleophile, the molar amount of solid phase amine should be in excess over the amount of crosslinker bound to the cell binding agent.

The cell-binding agent can be any suitable agent that binds to a cell, typically and preferably an animal cell (e.g., a human cell). The cell-binding agent preferably is a peptide or a polypeptide. Suitable cell-binding agents include, for example, antibodies (e.g., monoclonal antibodies and fragments thereof), lymphokines, hormones, growth factors, nutrient-transport molecules (e.g., transferrin), and any other agent or molecule that specifically binds a target molecule on the surface of a cell.

The term "antibody," as used herein, refers to any immunoglobulin, any immunoglobulin fragment, such as Fab, F(ab')$_2$, dsFv, sFv, diabodies, and triabodies, or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, Eur. J. Immunol., 5: 511-519 (1976), Harlow and Lane (eds.), Antibodies: A Laboratory Manual, CSH Press (1988), and C. A. Janeway et al. (eds.), Immunobiology, $5^{th}$ Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, J. Immunol. Methods, 74(2): 361-67 (1984), and Roder et al., Methods Enzymol., 121: 140-67 (1986)), bacteriophage vector expression systems (see, e.g., Huse et al., Science, 246: 1275-81 (1989)), or phage display libraries comprising antibody fragments, such as Fab and scFv (single chain variable region) (see, e.g., U.S. Pat. Nos. 5,885,793 and 5,969,108, and International Patent Applications WO 92/01047 and WO 99/06587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-drug conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, $3^{rd}$ Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235: 959-973 (1994). While the antibody employed in the conjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the $F(ab')_2$ fragment. Reduction of a $F(ab')_2$ fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, *J. Immunol.*, 131: 2895-2902 (1983), Spring et al., *J. Immunol.*, 113: 470-478 (1974), and Nisonoff et al., *Arch. Biochem. Biophys.*, 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., *Nature Struct. Biol.*, 3: 752, (1996)), or a shark antibody, such as, for example, a new antigen receptor (IgNAR) (see, e.g., Greenberg et al., *Nature*, 374: 168 (1995), and Stanfield et al., *Science*, 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., *Nature*, 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., *Leukemia Res.*, 8: 521 (1984)), and can be used to target cells that express CD33 (e.g., acute myelogenous leukemia (AML) cells).

Similarly, the monoclonal antibody anti-B4 (also referred to as B4) is a murine IgG1 antibody that binds to the CD19 antigen on B cells (Nadler et al., J. Immunol., 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the conjugate to target drugs to cells of neuroendocrine origin. The J5, MY9, and B4 antibodies preferably are resurfaced or humanized prior to their use as part of the conjugate. Resurfacing or humanization of antibodies is described in, for example, Roguska et al., *Proc. Natl. Acad. Sci. USA*, 91: 969-73 (1994).

In addition, the monoclonal antibody C242 binds to the CanAg antigen (see, e.g., U.S. Pat. No. 5,552,293), and can be used to target the conjugate to CanAg expressing tumors, such as colorectal, pancreatic, non-small cell lung, and gastric cancers. HuC242 is a humanized form of the monoclonal antibody C242 (see, e.g., U.S. Pat. No. 5,552,293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693,762) or resurfacing technology (see, e.g., U.S. Pat. No. 5,639,641). HuC242 can be used to target the conjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the conjugate. Anti-MUC1 antibodies include, for example, anti-HMFG-2 (see, e.g., Taylor-Papadimitriou et al., *Int. J. Cancer*, 28: 17-21 (1981)), hCTM01 (see, e.g., van Hof et al., *Cancer Res.*, 56: 5179-5185 (1996)), and DS6. Prostate cancer cells also can be targeted with the conjugate by using an anti-prostate-specific membrane antigen (PSMA) as the cell-binding agent, such as J591 (see, e.g., Liu et al., *Cancer Res.*, 57: 3629-3634 (1997)). Moreover, cancer cells that express the Her2 antigen, such as breast, prostate, and ovarian cancers, can be targeted using the antibody trastuzumab. Anti-IGF-IR antibodies that bind to insulin-like growth factor receptor also can be used in the conjugate.

Particularly preferred antibodies are humanized monoclonal antibodies, examples of which include huN901, huMy9-6, huB4, huC242, trastuzumab, bivatuzumab, sibrotuzumab, and rituximab (see, e.g., U.S. Pat. Nos. 5,639,641 and 5,665,357, U.S. Provisional Patent Application No. 60/424,332 (which is related to U.S. Patent Application Publication No. 2005/0118183 A1), International Patent Application WO 02/16401, Pedersen et al., supra, Roguska et al., supra, Liu et al., supra, Nadler et al., supra, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)). Most preferably, the antibody is the huN901 humanized monoclonal antibody or the huMy9-6 humanized monoclonal antibody. Other preferred antibodies include CNTO95, huDS6, huB4, and huC242. Other humanized monoclonal antibodies are known in the art and can be used in connection with the invention.

While the cell-binding agent preferably is an antibody, the cell-binding agent also can be a non-antibody molecule. Suitable non-antibody molecules include, for example, interferons (e.g., alpha, beta, or gamma interferon), lymphokines (e.g., interleukin 2 (IL-2), IL-3, IL-4, or IL-6), hormones (e.g., insulin), growth factors (e.g., EGF, TGF-alpha, FGF, and VEGF), colony-stimulating factors (e.g., G-CSF, M-CSF, and GM-CSF (see, e.g., Burgess, *Immunology Today*, 5: 155-158 (1984)), somatostatin, and transferrin (see, e.g., O'Keefe et al., *J. Biol. Chem.*, 260: 932-937 (1985)). For example, GM-CSF, which binds to myeloid cells, can be used as a cell-binding agent to target acute myelogenous leukemia cells. In addition, IL-2, which binds to activated T-cells, can be used for prevention of transplant graft rejection, for therapy and prevention of graft-versus-host disease, and for treatment of acute T-cell leukemia. Epidermal growth factor (EGF) can be used to target squamous cancers such as lung cancer and head and neck cancer. Somatostatin can be used to target neuroblastoma cells and other tumor cell types.

The conjugate can comprise any suitable drug, typically a cytotoxic agent. A "cytotoxic agent," as used herein, refers to any compound that results in the death of a cell, induces cell death, or decreases cell viability. Suitable cytotoxic agents include, for example, maytansinoids and maytansinoid analogs, taxoids, CC-1065 and CC-1065 analogs, and dolastatin and dolastatin analogs. In a preferred embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy/$CH_2OR$) (U.S. Pat. No. 4,331,598), (3) C-14-hydroxymethyl or acyloxymethyl ($CH_2OH$ or $CH_2OAc$) (U.S. Pat. No. 4,450,254) (prepared from *Nocardia*), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In a preferred embodiment of the invention, the conjugate utilizes the thiol-containing maytansinoid DM1, also known as $N^{2'}$-deacetyl-$N^{2'}$-(3-mercapto-1-oxopropyl)-maytansine, as the cytotoxic agent. The structure of DM1 is represented by formula (I):

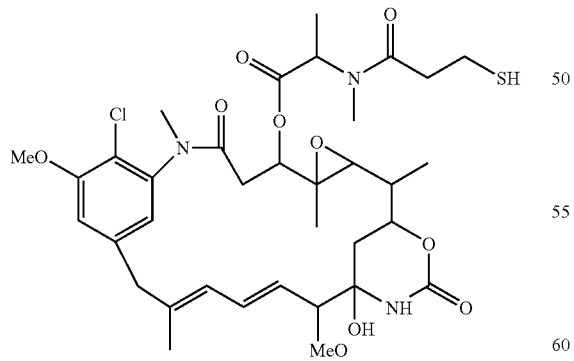

(I)

In another preferred embodiment of the invention, the conjugate utilizes the thiol-containing maytansinoid DM4, also known as $N^{2'}$-deacetyl-$N^{2'}$-(4-methyl-4-mercapto-1-oxopentyl)-maytansine, as the cytotoxic agent. The structure of DM4 is represented by formula (II):

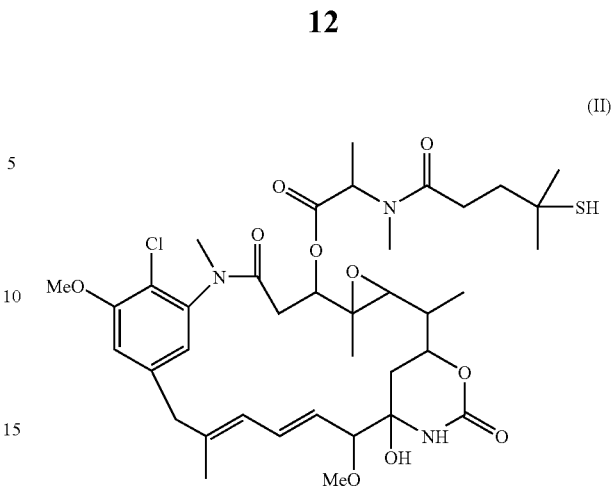

(II)

Other maytansines may be used in the context of the invention, including, for example, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansines for use in the context of the invention include compounds represented by formula (III):

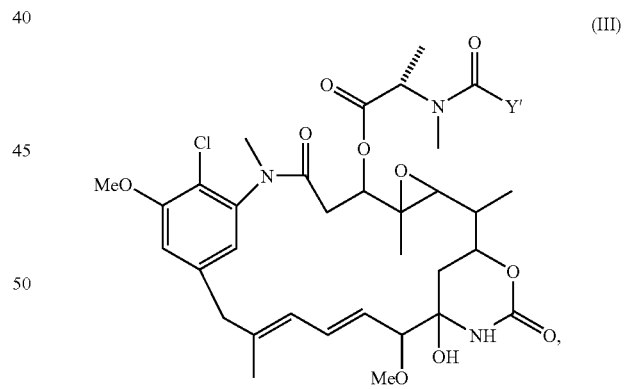

(III)

wherein Y' represents $(CR_7R_8)_l(CR_9=CR_{10})_pC\equiv C_qA_o(CR_5R_6)_mD_u(CR_{11}=CR_{12})_r(C\equiv C)_sB_t(CR_3R_4)_n$—$CR_1R_2SZ$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein A, B, D are cycloalkyl or cycloalkenyl having 3-10 carbon atoms, simple or substituted aryl, or heterocyclic aromatic, or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic, or heterocycloalkyl radical, wherein l, m, n, o, p, q, r, s, and t are each independently zero or an integer from 1 to 5, provided that at least two of l, m, n, o, p, q, r, s and t are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic, or heterocycloalkyl radical.

Preferred embodiments of formula (III) include compounds of formula (III) wherein (a) $R_1$ is H, $R_2$ is methyl and Z is H, (b) $R_1$ and $R_2$ are methyl and Z is H, (c) $R_1$ is H, $R_2$ is methyl, and Z is —$SCH_3$, and (d) $R_1$ and $R_2$ are methyl, and Z is —$SCH_3$.

Such additional maytansines also include compounds represented by formula (IV-L), (IV-D), or (IV-D,L):

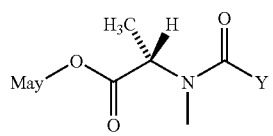

(IV-L)

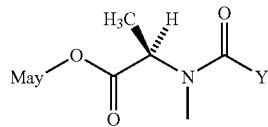

(IV-D)

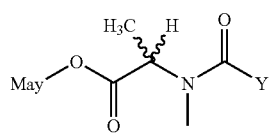

(IV-D,L)

wherein Y represents $(CR_7R_8)_l(CR_5R_6)_m(CR_3R_4)_n CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl.

Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, and $R_8$ are each H, l and m are each 1, n is 0, and Z is H, (b) $R_1$ and $R_2$ are methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Additional preferred maytansines also include compounds represented by formula (V):

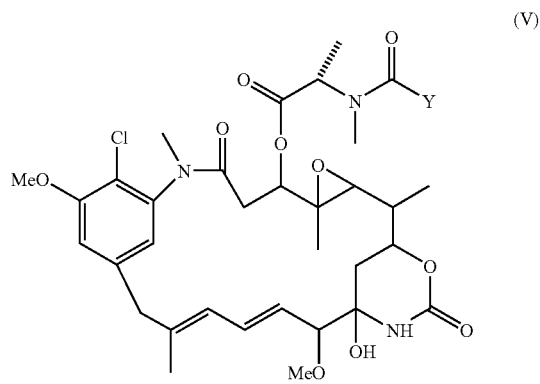

(V)

wherein Y represents $(CR_7R_8)_l(CR_5R_6)_m(CR_3R_4)_n CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, $R_8$ are each H, l and m are 1; n is 0; and Z is H, (c) $R_1$ is H, $R_2$ is methyl, $R_5$, $R_6$, $R_7$, and R are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Still further preferred maytansines include compounds represented by formula (VI-L), (VI-D), or (VI-D,L):

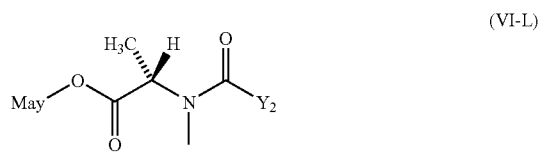

(VI-L)

-continued

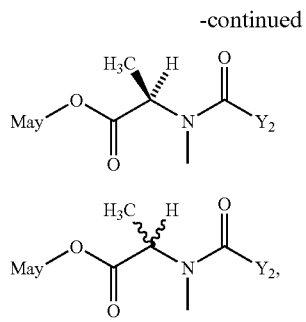

wherein $Y_2$ represents $(CR_7R_8)_l(CR_5R_6)_m(CR_3R_4)_n CR_1R_2SZ_2$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, and n are each independently an integer of from 1 to 5, and in addition n can be zero, wherein $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical, and wherein May is a maytansinoid.

Additional preferred maytansines include compounds represented by formula (VII):

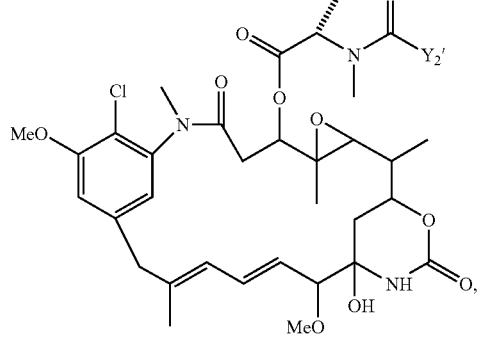

wherein $Y_{2'}$ represents $(CR_7R_8)_l(CR_9=CR_{10})_p(C\equiv C)_qA_o (CR_5R_6)_mD_u(CR_{11}=CR_{12})_r(C\equiv C)_sB_t(CR_3R_4)_nCR_1R_2SZ_2$, wherein $R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H, wherein A, B, and D each independently is cycloalkyl or cycloalkenyl having 3 to 10 carbon atoms, simple or substituted aryl, or heterocyclic aromatic or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, n, o, p, q, r, s, and t are each independently zero or an integer of from 1 to 5, provided that at least two of l, m, n, o, p, q, r, s and t are not zero at any one time, and wherein $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (VII) include compounds of formula (VII), wherein $R_1$ is H and $R_2$ is methyl.

In addition to maytansinoids, the cytotoxic agent used in the conjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

A preferred taxane for use in the preparation of a cytotoxic conjugate is the taxane of formula (VIII):

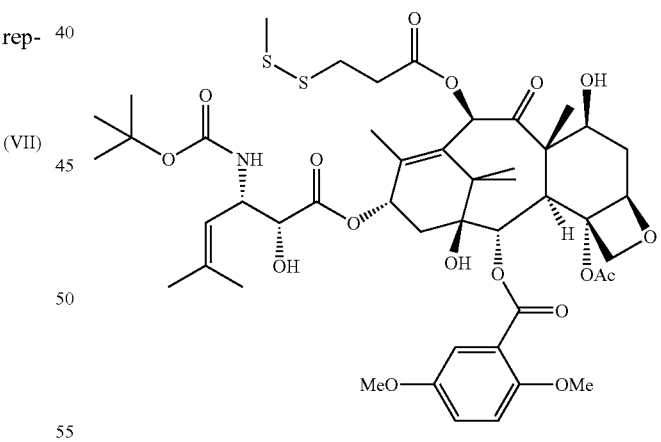

Methods for synthesizing taxanes that can be used in the context of the invention, along with methods for conjugating taxanes to cell-binding agents such as antibodies, are described in detail in U.S. Pat. Nos. 5,416,064, 5,475,092, 6,340,701, 6,372,738, 6,436,931, 6,596,757, 6,706,708, and 6,716,821, and in U.S. Patent Application Publication No. 2004/0024049 A1.

The cytotoxic also can be CC-1065 or a derivative thereof. CC-1065 is a potent anti-tumor antibiotic isolated from the culture broth of *Streptomyces zelensis*. CC-1065 is about 1000-fold more potent in vitro than commonly used anticancer drugs, such as doxorubicin, methotrexate, and vincristine (Bhuyan et al., *Cancer Res.*, 42: 3532-3537 (1982)). CC-1065 and its analogs are disclosed in U.S. Pat. Nos. 5,585,499, 5,846,545, 6,340,701, and 6,372,738. The cytotoxic potency of CC-1065 has been correlated with its alkylating activity and its DNA-binding or DNA-intercalating activity. These two activities reside in separate parts of the molecule. In this respect, the alkylating activity is contained in the cyclopropapyrroloindole (CPI) subunit and the DNA-binding activity resides in the two pyrroloindole subunits of CC-1065.

Several CC-1065 analogs are known in the art and also can be used as the cytotoxic agent in the conjugate (see, e.g., Warpehoski et al., *J. Med. Chem.*, 31: 590-603 (1988)). A series of CC-1065 analogs has been developed in which the CPI moiety is replaced by a cyclopropabenzindole (CBI) moiety (Boger et al., *J. Org. Chem.*, 55: 5823-5833 (1990), and Boger et al., *Bioorg. Med. Chem. Lett.*, 1: 115-120 (1991)). These CC-1065 analogs maintain the high in vitro potency of the parental drug, without causing delayed toxicity in mice. Like CC-1065, these compounds are alkylating agents that covalently bind to the minor groove of DNA to cause cell death.

The therapeutic efficacy of CC-1065 analogs can be greatly improved by changing the in vivo distribution through targeted delivery to a tumor site, resulting in lower toxicity to non-targeted tissues, and thus, lower systemic toxicity. To this end, conjugates of analogs and derivatives of CC-1065 with cell-binding agents that specifically target tumor cells have been generated (see, e.g., U.S. Pat. Nos. 5,475,092, 5,585, 499, and 5,846,545). These conjugates typically display high target-specific cytotoxicity in vitro, and anti-tumor activity in human tumor xenograft models in mice (see, e.g., Chari et al., *Cancer Res.*, 55: 4079-4084 (1995)).

Methods for synthesizing CC-1065 analogs are described in detail in U.S. Pat. Nos. 5,475,092, 5,585,499, 5,846,545, 6,534,660, 6,586,618, and 6,756,397 and U.S. Patent Application Publication No. 2003/0195365 A1.

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs also can be used in the context of the invention. Doxarubicin and daunorubicin compounds (see, e.g., U.S. Pat. No. 6,630,579) can also be used as the drug.

The drug conjugates may be prepared by in vitro methods. In order to link a drug or prodrug to the antibody, a linking group is used. Suitable linking groups are well known in the art and include disulfide groups, acid labile groups, photo-labile groups, peptidase labile groups, and esterase labile groups. Preferred linking groups are disulfide groups. For example, conjugates can be constructed using a disulfide exchange reaction between the antibody and the drug or prodrug. The drug molecules also can be linked to a cell-binding agent through an intermediary carrier molecule such as serum albumin.

In accordance with the invention, the cell-binding agent is modified by reacting a bifunctional crosslinking reagent with the cell-binding agent, thereby resulting in the covalent attachment of a linker molecule to the cell-binding agent. As used herein, a "bifunctional crosslinking reagent" is any chemical moiety that covalently links a cell-binding agent to a drug, such as the drugs described herein. In a preferred embodiment of the invention, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

Any suitable bifunctional crosslinking reagent can be used in connection with the invention, so long as the linker reagent provides for retention of the therapeutic, e.g., cytotoxicity, and targeting characteristics of the drug and the cell-binding agent, respectively. Preferably, the linker molecule joins the drug to the cell-binding agent through chemical bonds (as described above), such that the drug and the cell-binding agent are chemically coupled (e.g., covalently bonded) to each other. Preferably, the linking reagent is a cleavable linker. More preferably, the linker is cleaved under mild conditions, i.e., conditions within a cell under which the activity of the drug is not affected. Examples of suitable cleavable linkers include disulfide linkers, acid labile linkers, photo-labile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., Proc. Natl. Acad. Sci. USA, 79: 626-629 (1982), and Umemoto et al., Int. J. Cancer, 43: 677-684 (1989)).

Preferably the drug is linked to a cell-binding agent through a disulfide bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group, that can react with the drug to form a disulfide bond. Particularly preferred linker molecules include, for example, N-succinimidyl 3-(2-pyridyldithio)propionate (SPDP) (see, e.g., Carlsson et al., *Biochem. J.*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and other reactive cross-linkers which are described in U.S. Pat. No. 6,913,748, which is incorporated herein in its entirety by reference.

While cleavable linkers preferably are used in the inventive method, a non-cleavable linker also can be used to generate the above-described conjugate. A non-cleavable linker is any chemical moiety that is capable of linking a drug, such as a maytansinoid, a taxane, or a CC-1065 analog, to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the drug or the cell-binding agent remains active.

Suitable crosslinking reagents that form non-cleavable linkers between a drug and the cell-binding agent are well known in the art. Examples of non-cleavable linkers include linkers having an N-succinimidyl ester or N-sulfosuccinimidyl ester moiety for reaction with the cell-binding agent, as well as a maleimido- or haloacetyl-based moiety for reaction with the drug. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

$$HOOC—X_l—Y_n—Z_m-COOH \qquad (IX),$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. patent application Ser. No. 10/960,602, which corresponds to U.S. Patent Application Publication No. 2005/0169933 A1.

Alternatively, as disclosed in U.S. Pat. No. 6,441,163 B1, the drug can be first modified to introduce a reactive ester suitable to react with a cell-binding agent. Reaction of these maytansinoids containing an activated linker moiety with a cell-binding agent provides another method of producing a cleavable or non-cleavable cell-binding agent maytansinoid conjugate.

Additional information concerning maytansinoids, cytotoxic agents comprising same, drug conjugates, and related preparation methods is disclosed in U.S. patent application Ser. No. 11/352,121 and U.S. patent application Ser. No. 10/849,136, which corresponds to U.S. Patent Application Publication No. 2004/0235840 A1.

The following examples further illustrate the invention but, of course, should not be construed as in any way limiting its scope.

EXAMPLE 1

This example demonstrates the purification of an antibody modified with a heterobifunctional modification reagent using TFF.

The huN901 monoclonal antibody (final concentration of 8 mg/ml) was incubated with N-succinimidyl 4-(2-pyridyldithio)pentanoate (SPP, 5.6-fold molar excess) for approximately 180 minutes at 20° C. in 50 mM potassium phosphate buffer (pH 7.5) containing 50 mM NaCl, 2 mM EDTA, and 5% ethanol. In a first group, the reaction mixture was purified using a column of Sephadex™ G25F resin equilibrated and eluted in 50 mM potassium phosphate buffer (pH 6.5) containing 50 mM NaCl and 2 mM EDTA. In a second group, the reaction mixture was purified using a Pellicon XL TFF system (Millipore, Billerica, Mass.), and the antibody was diafiltered (5 volumes) into 50 mM potassium phosphate, 50 mM NaCl (pH 6.5), and 2 mM EDTA using a 10,000 molecular weight cutoff membrane (Ultracel™ regenerated cellulose membrane, Millipore, Billerica, Mass.). Both samples were conjugated with DM1 (1.7 fold molar excess over the unbound linker) for 18 hours at pH 6.5 in potassium phosphate buffer containing 50 mM NaCl and a final concentration of 3% DMA.

In both groups, yields were determined spectrophotometrically (wavelength 280 nm) for the combined modification and purification step. Linker/antibody ratios were also determined by treatment with dithiothreitol to release pyridine-2-thione, which has an extinction coefficient of 8,080 $M^{-1}cm^{-1}$ at 343 nM. Drug/antibody ratios were determined spectrophotometrically (wavelengths of 280 nm and 252 nm) for the conjugation step. In addition, the removal of SPP-related small molecule species was measured by Hisep HPLC.

The resulting data are set forth in Table 1.

TABLE 1

| Purification Methods for Modified huN901 Using G-25F versus TFF | | | |
|---|---|---|---|
| | | Sephadex ™ G25F Resin | TFF |
| Modification Step | Step yield | 94% | 98% |
| | Linker/Antibody ratio | 4.9 | 4.9 |
| | SPP-related small molecules | 0.2% | 0.2% |
| Conjugation Step | Drug/Antibody ratio | 3.7 | 3.7 |

As shown in Table 1, the use of TFF yields drug conjugate product of at least equivalent quality to the nonadsorptive chromatography (G25) process while being more convenient and scaleable.

EXAMPLE 2

This example demonstrates the purification of an antibody modified with a heterobifunctional modification reagent using adsorptive chromatography.

The huB4 antibody was modified with N-succinimidyl 4-(2-pyridyldithio)butanoate (SPDB, 5.4 fold molar excess) for 120 minutes at room temperature in 50 mM potassium phosphate buffer (pH 6.5) containing 50 mM NaCl, 2 mM EDTA, and 5% ethanol. In a first group, the reaction mixture was purified using the Sephadex™ G25F resin as described in Example 1. In a second group, the reaction mixture was loaded onto a column of ceramic hydroxyapatite (CHT, Bio-Rad Laboratories, Hercules, Calif.), which was equilibrated in 12.5 mM potassium phosphate buffer (pH 6.5) and eluted with 80 mM potassium phosphate buffer (pH 6.5).

In both groups, yields and linker/antibody ratios were determined as described in Example 1. The first group had a 91% yield and 4.2 linker/antibody ratio. The second group had a 89% yield and a 4.2 linker/antibody ratio.

The CNTO95 antibody (final concentration of 10 mg/ml) was modified with N-succinimidyl 4-(2-pyridyldithio)butanoate (SPDB, 4.5 fold molar excess) for 120 minutes at 20° C. in 10 mM sodium phosphate buffer (pH 7.5) containing 2.7% sucrose and 5% ethanol. In a first group, the reaction mixture was purified using Sephadex™ G25F resin in 12.5 mM potassium phosphate buffer (pH 6.6) containing 12.5 mM NaCl and 0.5 mM EDTA. In a second group, the reaction mixture was loaded onto a column of SP Sepharose Fast Flow (GE Healthcare, Piscataway, N.J.), which was equilibrated in 10 mM sodium phosphate buffer (pH 7.5) and eluted with 50 mM potassium phosphate buffer (pH 7.5), containing 50 mM NaCl.

In both groups, yields and linker/antibody ratios were determined as described in Example 1. The first group had an 96% yield and 4.0 linker/antibody ratio. The second group had a 97% yield and a 4.1 linker/antibody ratio.

The data obtained in this example demonstrate that adsorptive chromatography can be used to purify an antibody modified with a heterobifunctional modification reagent.

EXAMPLE 3

This example demonstrates the beneficial effects of conjugating a modified antibody with a drug at a pH of above 6.5.

In a first experiment, CNTO95 antibody was modified and purified as described in Example 2. The modified antibody was then divided into two groups. In the first group, conjugation was performed in 12.5 mM potassium phosphate at pH 6.5 containing 12.5 mM NaCl, 0.5 mM EDTA, 3% DMA, and 1.7 fold molar excess drug per linker at 20° C. In the second group, the conjugation reaction was at pH 7.5. The conjugated antibody was purified over NAP-10 columns.

The drug/antibody ratio was measured for both groups. The resulting data are set forth in Table 2.

TABLE 2

Drug/Antibody Ratio at Conjugation Reaction of pH 6.5 versus 7.5

| Reaction Time (hours) | Drug/Antibody Ratio at Conjugation Reaction pH 6.5 | Drug/Antibody Ratio at Conjugation Reaction pH 7.5 |
| --- | --- | --- |
| 0.5 | — | 3.0 |
| 1 | 2.3 | 3.4 |
| 1.5 | — | 3.5 |
| 2 | 2.8 | 3.5 |
| 2.75 | — | 3.6 |
| 3.5 | 3.2 | 3.6 |
| 5 | 3.4 | 3.7 |

As shown by the data set forth in Table 2, conjugation proceeds faster at pH 7.5 than at pH 6.5.

In a second experiment, huB4 humanized monoclonal antibody was modified with either (a) a 4.9-fold molar excess of SPDB relative to antibody, or (b) a 4.8-fold molar excess of SPDB relative to antibody. In both situations, reaction was in 50 mM potassium phosphate, 50 mM potassium chloride, and 2 mM EDTA (pH 6.5) in 5% ethanol for a total of 120 minutes at room temperature. Sample (a) was purified over a column of Sephadex™ G25F resin equilibrated in 50 mM potassium phosphate, 50 mM sodium chloride, and 2 mM EDTA at pH 6.5. Sample (b) was purified equivalently except that the chromatography buffer was adjusted to pH 7.5. Both samples were conjugated with DM4 (1.7 fold molar excess over bound linker) for 18 hours at room temperature in a final concentration of dimethylacetamide (DMA) of 3%.

Thus, sample (a) was conjugated at pH 6.5, and sample (b) was conjugated at pH 7.5. The samples were then purified over a column of Sephadex™ G25F resin equilibrated in 9.6 mM potassium phosphate and 4.2 mM sodium chloride at pH 6.5. Both samples were incubated at 4° C. for up to 7 months and subjected to analysis of released free drug at intervals. The resulting data are set forth in Table 3.

TABLE 3

Release of Free Drug Over Time from Samples Conjugated at pH 6.5 and 7.5

| Time (months) | pH 6.5 Conjugation | pH 7.5 Conjugation |
| --- | --- | --- |
| 0 | 1.0 | 0.8 |
| 1.5 | 1.8 | 1.0 |
| 2.5 | 3.2 | 1.9 |
| 7 | 4.0 | 2.8 |

As shown by the data set forth in Table 3, release of free drug is substantially slower from sample (b) that had been conjugated at pH 7.5 relative to sample (a) that had been conjugated at pH 6.5. Accordingly, drug conjugate product prepared at pH 7.5 is shown to be more stable with respect to release of free drug over time as compared to the drug conjugate product prepared at pH 6.5. The conjugation at pH 7.5 also shows a better drug incorporation than at pH 6.5, thereby requiring less drug to be used.

EXAMPLE 4

This example demonstrates the beneficial effects of conjugating a modified antibody with a drug at a pH of below 6.0.

The huN901 monoclonal antibody (final concentration of 8 mg/ml) was incubated with N-succinimidyl 4-(2-pyridyldithio)pentanoate (SPP, 5.6-fold molar excess) for approximately 180 minutes at 20° C. in 50 mM potassium phosphate buffer (pH 7.5) containing 50 mM NaCl, 2 mM EDTA, and 5% ethanol. In a first group, the reaction mixture was purified using a column of Sephadex™ G25F resin equilibrated and eluted in 50 mM sodium citrate buffer (pH 5.0) containing 50 mM NaCl and 2 mM EDTA. In a second group, the reaction mixture was purified using a column of Sephadex™ G25F resin equilibrated and eluted in 50 mM potassium phosphate buffer (pH 6.5) containing 50 mM NaCl and 2 mM EDTA. Both samples were conjugated with DM4 (1.7-fold molar excess over bound linker) for 3, 19, 25, 48, and 120 hours at room temperature in a final concentration of dimethylacetamide (DMA) of 3%.

Thus, the first group of samples was conjugated in 50 mM sodium citrate buffer (ph 5.0) containing 50 mM NaCl and 2 mM EDTA, and the second group of samples was conjugated in 50 mM sodium phosphate buffer (pH 6.5), containing 50 mM NaCl and 2 mM EDTA. The samples were then purified using a column of Sephadex™ G25F resin equilibrated and eluted in 50 mM potassium phosphate buffer (pH 6.5) containing 50 mM NaCl.

In both groups, linker/antibody ratios were determined by treatment with dithiothreitol to release pyridine-2-thione, which has an extinction coefficient of 8,080 $M^{-1}cm^{-1}$ at 343 nM. Drug/antibody ratios were determined spectrophotometrically (wavelengths of 280 nm and 252 nm) for the conjugation step.

The first group had a 4.3 linker/antibody ratio. The second group had a 4.2 linker/antibody ratio.

The drug/antibody ratios over time for the two groups are set forth in Table 4.

TABLE 4

Rate of Incorporation of DM1 into SPP-modified huN901 as a Function of Conjugation pH

| | Drug/Antibody Ratio (mol/mol) | |
|---|---|---|
| Reaction Time (hours) | pH 5.0 Conjugation | pH 6.5 Conjugation |
| 3 | 2.43 | 2.97 |
| 19 | 3.38 | 3.28 |
| 25 | 3.41 | NT |
| 48 | 3.46 | 3.17 |
| 120 | 3.44 | 2.85 |

As is apparent from the data set forth in Table 4, conjugate that is made by conjugating the modified antibody with the drug at a pH of 5.0 reaches a higher and more stable level of bound drug during the course of the conjugation reaction than conjugate made at a conjugation pH of 6.5. In addition to increased stability, the results indicate that a higher drug/antibody level is achieved upon conjugation at pH 5.0 than when using the same amount of drug at a conjugation pH of 6.5, thereby indicating more efficient usage of drug at pH 5.0.

In both groups, the conjugate monomer amounts were determined over time. The resulting data are set forth in Table 5.

TABLE 5

Effect of Conjugation pH on Level of Conjugate Monomer During Conjugation of SPP-modified huN901 with DM1

| | Conjugate Monomer (%) | |
|---|---|---|
| Reaction Time (hours) | pH 5.0 Conjugation | pH 6.5 Conjugation |
| 3 | 98.5 | 98.0 |
| 19 | 98.8 | 98.2 |
| 25 | 99.1 | NT |
| 48 | 99.2 | 98.3 |
| 120 | 99.2 | 97.8 |

As is apparent from the data set forth in Table 5, conjugate that is made by conjugating the modified antibody with the drug at a pH of 5.0 has a higher level of conjugate monomer than conjugate made at a conjugation pH of 6.5.

EXAMPLE 5

This example further demonstrates benefits of conjugating a drug to a modified antibody at a pH of less than 6.

BIWA 4 antibody was modified with SPP (molar excess of SPP as shown in Table 6) for 120-140 minutes at room temperature in 50 mM potassium phosphate buffer (pH 6.5), 50 mM NaCl, 2 mM EDTA, and 5% ethanol. Aliquots of modified antibody were purified on separate NAP 25 columns equilibrated in buffers having various pH values (pH 4.6-6.5). The pH 4.6-5.9 buffers were composed of 35 mM sodium citrate, 150 mM sodium chloride, and 2 mM EDTA. The pH 6.5 buffer was PBS with 2 mM EDTA.

Modified antibody at each pH was conjugated with DM1 (1.7 fold molar excess over linker) in dimethylacetamide (DMA, final concentration of 3%). After incubation for 17-18 hours at room temperature, the conjugated antibody samples were purified by chromatography on NAP 25 columns equilibrated in PBS (pH 6.5). Linker/antibody ratios (L/A in Table 6) were determined by treatment with dithiothreitol to release pyridine-2-thione, which has an extinction coefficient of 8,080 $M^{-1}cm^{-1}$ at 343 nM. Drug/antibody ratios were determined spectrophotometrically (wavelengths of 280 nm and 252 nm) for the conjugation step. Conjugate monomer, high molecular weight species, and low molecular weight species were determined by SEC-HPLC using a TSKG3000SWXL column equilibrated and developed in 0.2 M potassium phosphate buffer (pH 7.0) containing 0.2 M potassium chloride and 20% isopropanol.

The results of this analysis are set forth in Table 6.

TABLE 6

Drug Conjugate Product Characteristics Relative to pH

| Buffer | SPP Molar Excess | L/A | D/A | Monomer (%) | High MW (%) | Low MW (%) | Conjugation Step Yield (%) |
|---|---|---|---|---|---|---|---|
| pH 4.6 | 4.7 | 3.8 | 3.6 | 97.5 | 2.2 | 0.4 | 74 |
| pH 5.1 | 4.4 | 4.7 | 3.6 | 97.6 | 1.9 | 0.6 | 75 |
| pH 5.6 | 5.0 | 4.9 | 3.6 | 97.7 | 1.5 | 0.8 | 85 |
| pH 5.9 | 5.5 | 5.3 | 3.7 | 96.4 | 2.3 | 1.4 | 76 |
| pH 6.5 | 6.6 | 6.4 | 3.7 | 95.1 | 2.8 | 1.9 | 71 |

The data set forth in Table 6 demonstrate that conjugation of SPP-modified BIWA 4 with DM1 was efficient at a pH below 6.0, compared with conjugation at pH 6.5. The amounts of linker and drug, specifically SPP linker and DM1, required to reach a particular final drug/antibody ratio was reduced at lower pH. In addition, levels of conjugate monomer, high molecular weight species, and low molecular weight species were more optimal, and yields were improved, at lower pH.

EXAMPLE 6

This example demonstrates that the step for purifying the modified antibody may optionally be eliminated. The drug may be added simultaneously with the bifunctional modifying reagent or at some later time.

In an example of addition of drug after the modifying reagent, the humanized monoclonal antibody CNTO95 was modified at a concentration of 20 mg/mL with the bifunctional modifying reagent SPDB at a molar excess of SPDB over antibody of 4.6 for 120 min at 20° C. The modification buffer was 44 mM phosphate buffer (pH 7.5) containing 5.3% sucrose and 5% ethanol. One aliquot of the modified antibody was purified over Sephadex™ G25F resin (standard four-step process), equilibrated and eluted in 12.5 mM potassium phosphate buffer (pH 7.5) containing 12.5 mM NaCl, and was subsequently conjugated with DM4 (1.7 fold molar excess of drug over bound linker) at a final modified antibody concentration of 10 mg/mL in 12.5 mM potassium phosphate buffer (pH 7.5) containing 12.5 mM NaCl and 10% DMA for 20 hours at room temperature. A second aliquot of the modified antibody was conjugated immediately at the end of the 120 minute modification reaction (three-step process), without being further purified.

The protein and buffer concentrations of the modification reaction mixture were adjusted to yield a modified protein concentration of 10 mg/mL and a buffer composition of 28 mM potassium phosphate (pH 7.5) containing 5.9 mM NaCl and 2.7% sucrose. DM4 was then added (1.7 fold molar excess over starting SPDB), and DMA was adjusted to a final concentration of 10%. After 20 hours incubation at room temperature, both aliquots of conjugated antibody were purified on Sephadex™ G25F resin equilibrated in 10 mM histidine and 10% sucrose at pH 5.5

Linker/antibody ratios (L/A) were determined by treatment with dithiothreitol to release pyridine-2-thione, which has an extinction coefficient of 8,080 $M^{-1}cm^{-1}$ at 343 nM. Drug/antibody (D/A) ratios and yield were determined spectrophotometrically (wavelengths of 280 nm and 252 nm) for the conjugation step. Percentages of monomer were assayed by SEC-HPLC. Percentages of free drug were assayed by HPLC on a Hisep column. The results of these analyses are set forth in Table 7.

TABLE 7

Optional Elimination of Purification Step for Modified Antibody

| Parameters | 4-step Process | 3-step Process |
|---|---|---|
| Starting SPDB | 4.6 x | 4.6 x |
| L/A | 4.1 | Not Determined |
| D/A | 3.9 | 4.0 |
| Yield | 79% | 91% |
| % Monomer | 95.8% | 96.1% |
| % Free Drug | 2.4% | 1.1% |

As demonstrated by the results set forth in Table 7, the step for purifying the modified antibody can be eliminated in the context of the invention.

EXAMPLE 7

This example demonstrates an improved means of purifying antibody that has been modified with a heterobifunctional modification reagent and then conjugated with a maytansinoid.

The huN901 antibody modified with SPP (7 fold molar excess) and purified on Sephadex™ G25F resin, as described in Example 1, was conjugated with the maytansinoid DM1 (1.7 fold molar excess over linker, dissolved in dimethylacetamide (DMA), 3% final concentration).

A first sample of conjugate was purified by standard chromatography on Sephadex™ G25F resin in phosphate buffered saline (PBS, pH 6.5).

A second conjugate sample was purified by a Pellicon XL TFF system (Millipore, Billerica, Mass.), as described in Example 1

A third conjugate sample was purified using a column of MEP Hypercell resin equilibrated in 50 mM Tris (pH 8.0), and eluted with 50 mM sodium acetate (pH 4.0).

A fourth conjugate sample was purified using a column of UNOsphere S resin equilibrated in 50 mM sodium phosphate (pH 6.5) and eluted with 0.2 M NaCl and 50 mM sodium phosphate (pH 6.5).

A fifth conjugate sample was purified using a column of CHT resin (Bio-Rad Laboratories, Hercules, Calif.) equilibrated in 50 mM sodium phosphate (pH 6.5) and eluted with 0.3 M NaCl and 50 mM sodium phosphate (pH 6.5).

A sixth conjugate sample was purified using a column of SP Sepharose resin equilibrated in 35 mM sodium citrate, 10 mM sodium chloride (pH 5.0), and eluted with 0.25 M NaCl, 35 mM sodium citrate (pH 5.0).

Conjugate monomer was determined by SEC-HPLC using a column of TSKG3000SW$_{XL}$ resin equilibrated and developed in 0.2 M potassium phosphate buffer at pH 7.0, containing 0.2 M potassium chloride and 20% isopropanol. The conjugation step yield was determined by dividing the yield of conjugated antibody by the amount of modified antibody that was conjugated (determined spectrophotometrically at a wavelength of 280 nm).

The results of these analyses are set forth in Table 8.

TABLE 8

Conjugation Purification Step Comparison

| Conjugate Sample | Conjugation Purification Step | Conjugate Monomer % | Step Yield % |
|---|---|---|---|
| 1 (control) | G25F resin | 93.2 | 86 |
| 2 (invention) | TFF | 92.8 | 85 |
| 3 (invention) | MEP Hypercell resin | 94.5 | 74 |
| 4 (invention) | UNOsphere resin | 96.3 | 81 |
| 5 (invention) | CHT resin | 97.9 | 72 |
| 6 (invention) | SP Sepharose resin | 95.1 | 81 |

The results in Table 8 show that all of the inventive purification methods (groups 2-6) gave similar yields to those obtained with the control process (group 1). Each inventive chromatographic method yielded an improvement in the level of conjugate monomer and may be readily scaled up.

In addition to CHT (ceramic hydroxyapatite), CFT (ceramic fluoroapatite) also can be used under similar chromatographic conditions. Alternatively both the CHT and CFT resins may be used in non-adsorptive mode so that the desired product (substantially monomeric conjugate) is not retained by the resins, whereas high molecular weight species are retained and thereby separated from the desired product.

Although a standard buffer/solvent composition for conjugation comprises 3% DMA, 50 mM potassium phosphate, 50 mM NaCl, and 2 mM EDTA at pH 6.5 (as utilized in Example 1), other compositions are more compatible with some of the chromatographic steps described herein and provide other benefits relative to the standard process. For instance, conjugation may be performed in 3% DMA, 12.5 mM potassium phosphate, 12.5 mM NaCl, and 0.5 mM EDTA at pH 6.5. Under these conditions, the amount of DM4 incorporated relative to the amount of linker incorporated in huB4 antibody was about 10% higher than for the standard conditions. In addition, these conditions are more compatible with loading onto resins such as cation exchange and CHT resins.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for preparing a cell-binding agent-cytotoxic agent conjugate comprising the steps of:
   (a) contacting a cell-binding agent with a bifunctional crosslinking reagent to covalently attach a linker to the cell-binding agent and thereby prepare a first mixture comprising cell-binding agents having linkers bound thereto, wherein the cell-binding agent is selected from the group consisting of antibodies, interferons, interleukin 2 (IL-2), interleukin 3 (IL-3), interleukin 4 (IL-4), interleukin 6 (IL-6), insulin, EGF, TGF-α, FGF, G-CSF, VEGF, MCSF, GM-CSF, and transferrin,
   (b) subjecting the first mixture to tangential flow filtration and thereby prepare a purified first mixture of cell-binding agents having linkers bound thereto,
   (c) conjugating a cytotoxic agent to the cell-binding agents having linkers bound thereto in the purified first mixture by reacting the cell-binding agents having linkers bound thereto with a cytotoxic agent in a solution having a pH of about 4 to about 9 to prepare a second mixture comprising (i) cell-binding agent chemically coupled through the linker to the cytotoxic agent, (ii) free cytotoxic agent, and (iii) reaction by-products produced during step (c), wherein the cytotoxic agent is selected from the group consisting of maytansinoids, taxanes, and CC1065, and
   (d) subjecting the second mixture to tangential flow filtration to purify the cell-binding agents chemically coupled through the linkers to the cytotoxic agent from the other components of the second mixture and thereby prepare a purified second mixture of cell-binding agents chemically coupled through the linkers to the cytotoxic agent.

2. The process of claim 1, wherein the solution in step (c) has a pH of from 4 to less than 6.0.

3. The process of claim 1, wherein the solution in step (c) has a pH of from greater than 6.5 to 9.

4. The process of claim 1, wherein the solution in step (c) has a pH of less than 6 or a pH of greater than 6.5.

5. The process of claim 1, wherein the cell-binding agent is an antibody.

6. The process of claim 5, wherein the antibody is a monoclonal antibody.

7. The process of claim 6, wherein the antibody is a humanized monoclonal antibody.

8. The process of claim 7, wherein the antibody is selected from the group consisting of huN901, huMy9-6, huB4, huC242, trastuzumab, bivatuzumab, sibrotuzumab, CNTO95, huDS6, and rituximab.

9. The process of claim 1, wherein the cytotoxic agent is a maytansinoid.

10. The process of claim 9, wherein the maytansinoid comprises a thiol group.

11. The process of claim 10, wherein the maytansinoid is DM1.

12. The process of claim 10, wherein the maytansinoid is DM4.

13. The process of claim 1, wherein the cell-binding agent is chemically coupled to the cytotoxic agent via chemical bonds selected from the group consisting of disulfide bonds, acid labile bonds, photolabile bonds, peptidase labile bonds, thioether bonds, and esterase labile bonds.

14. The process of claim 1, wherein the solution in step (c) comprises sucrose.

15. The process of claim 1, wherein the solution in step (c) further comprises a buffering agent selected from the group consisting of a citrate buffer, an acetate buffer, a succinate buffer, and a phosphate buffer.

16. The process of claim 1, further comprising
   (e) holding the mixture between at least one of steps a-b, steps b-c, and steps c-d to release the unstably bound linkers from the cell-binding agent.

17. The process of claim 16, wherein the mixture is held between steps a-b.

18. The process of claim 16, wherein the mixture is held between steps b-c.

19. The process of claim 16, wherein the mixture is held between steps c-d.

20. A process for preparing a cell-binding agent cytotoxic agent conjugate comprising the steps of:
   (a) contacting a cell-binding agent with a bifunctional crosslinking reagent to covalently attach a linker to the cell-binding agent and thereby prepare a first mixture comprising cell-binding agents having linkers bound thereto, wherein the cell-binding agent is selected from the group consisting of antibodies, interferons, interleukin 2 (IL-2), interleukin 3 (IL-3), interleukin 4 (IL-4), interleukin 6 (IL-6), insulin, EGF, TGF-α, FGF, G-CSF, VEGF, MCSF, GM-CSF, and transferrin,
   (b) conjugating a cytotoxic agent to the cell-binding agents having linkers bound thereto in the first mixture by reacting the cell-binding agent having linkers bound thereto with a cytotoxic agent in a solution having a pH of about 4 to about 9 to prepare a second mixture comprising (i) cell-binding agent chemically coupled through the linker to the cytotoxic agent, (ii) free cytotoxic agent, and (iii) reaction by-products produced during step (b), and
   (c) subjecting the second mixture to tangential flow filtration, selective precipitation, adsorptive filtration, adsorptive chromatography, or a combination thereof, to purify the cell-binding agents chemically coupled through the linkers to the cytotoxic agent from the other components of the second mixture and thereby prepare a purified second mixture of cell-binding agents chemically coupled through the linkers to the cytotoxic agent with the proviso that the first mixture is not subjected to tangential flow filtration, selective precipitation, adsorptive filtration, or adsorptive chromatography.

21. The process of claim 20, wherein the first mixture is not subjected to purification.

22. The process of claim 20, wherein the adsorptive chromatography is selected from the group consisting of hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof.

23. The process of claim 20, wherein the solution in step (b) has a pH of from about 4 to about 6.

24. The process of claim 20, wherein the solution in step (b) has a pH of from about 6.5 to about 9.

25. The process of claim 20, wherein the solution in step (b) has a pH of less than 6.0 or a pH of greater than 6.5.

26. The process of claim 20, wherein the cell-binding agent is an antibody.

27. The process of claim 26, wherein the antibody is a monoclonal antibody.

28. The process of claim 26, wherein the antibody is a humanized monoclonal antibody.

29. The process of claim 28, wherein the antibody is selected from the group consisting of huN901, huMy9-6, huB4, huC242, trastuzumab, bivatuzumab, sibrotuzumab, CNTO95, huDS6, and rituximab.

30. The process of claim 20, wherein the cytotoxic agent is selected from the group consisting of maytansinoids, taxanes, and CC1065.

31. The process of claim 30, wherein the cytotoxic agent is a maytansinoid.

32. The process of claim 31, wherein the maytansinoid comprises a thiol group.

33. The process of claim 32, wherein the maytansinoid is DM1.

34. The process of claim 32, wherein the maytansinoid is DM4.

35. The process of claim 20, wherein the cell-binding agent is chemically coupled to the cytotoxic agent via chemical bonds selected from the group consisting of disulfide bonds, acid labile bonds, photolabile bonds, peptidase labile bonds, thioether bonds, and esterase labile bonds.

36. The process of claim 20, wherein the solution in step (b) comprises sucrose.

37. The process of claim 20, wherein the solution in step (b) further comprises a buffering agent selected from the group consisting of a citrate buffer, an acetate buffer, a succinate buffer, and a phosphate buffer.

38. The process of claim 20, further comprising
  (e) holding the mixture between at least one of steps a-b and steps b-c to release the unstably bound linkers from the cell-binding agent.

39. The process of claim 38, wherein the mixture is held between steps a-b.

40. The process of claim 38, wherein the mixture is held between steps b-c.

* * * * *